US00PP25355P2

(12) United States Plant Patent
Pieters

(10) Patent No.: US PP25,355 P2
(45) Date of Patent: Mar. 17, 2015

(54) ***CHRYSANTHEMUM* PLANT NAMED 'YELLOW SAN REMO RUNNER'**

(50) Latin Name: *Chrysanthemum×morifolium*
Varietal Denomination: Yellow San Remo Runner

(71) Applicant: Luc Remi Johan Pieters, Staden-Oostnieuwkerke (BE)

(72) Inventor: Luc Remi Johan Pieters, Staden-Oostnieuwkerke (BE)

(73) Assignee: Pieters Joseph & Luc B.V.B.A., Staden-Oostnieuwkerke (BE)

( * ) Notice: Subject to any disclaimer, the term of this patent is extended or adjusted under 35 U.S.C. 154(b) by 127 days.

(21) Appl. No.: 13/815,611

(22) Filed: Mar. 11, 2013

(51) Int. Cl.
*A01H 5/00* (2006.01)

(52) U.S. Cl.
USPC ..... Plt./295

(58) Field of Classification Search
USPC ..... Plt./295
See application file for complete search history.

*Primary Examiner* — Susan McCormick Ewoldt
(74) *Attorney, Agent, or Firm* — C. A. Whealy

(57) ABSTRACT

A new and distinct cultivar of *Chrysanthemum* plant named 'Yellow San Remo Runner', characterized by its uniform, upright, outwardly spreading and mounding plant habit; moderately vigorous growth habit; freely branching habit; dense and full plant habit; uniform and freely flowering habit; large decorative-type inflorescences with bright yellow-colored ray florets; and good garden performance.

2 Drawing Sheets

Botanical designation: *Chrysanthemum×morifolium.*

Cultivar denomination: 'YELLOW SAN REMO RUNNER'.

CROSS-REFERENCED TO CLOSELY-RELATED APPLICATIONS

Title: *Chrysanthemum* Plant Named 'Red San Remo Runner'

Applicant: Luc Remi Johan Pieters

Filed: Concurrently with this application, U.S. Plant patent application Ser. No. 13/815,609

BACKGROUND OF THE INVENTION

The present invention relates to a new and distinct cultivar of *Chrysanthemum* plant, botanically known as *Chrysanthemum×morifolium* and hereinafter referred to by the name 'Yellow San Remo Runner'.

The new *Chrysanthemum* plant is a naturally-occurring whole plant mutation of *Chrysanthemum×morifolium* 'Bronze San Remo Runner', disclosed in U.S. Plant Pat. No. 23,319. The new *Chrysanthemum* plant was discovered and selected by the Inventor as a flowering plant from within a population of plants of 'Bronze San Remo Runner' in a controlled greenhouse environment in Staden-Oostnieuwkerke, Belgium in October, 2009.

Asexual reproduction of the new *Chrysanthemum* plant by vegetative cuttings was first conducted in a controlled greenhouse environment in Staden-Oostnieuwkerke, Belgium in January, 2010. Asexual reproduction by cuttings has shown that the unique features of this new *Chrysanthemum* plant are stable and reproduced true to type in successive generations.

SUMMARY OF THE INVENTION

Plants of the new *Chrysanthemum* have not been observed under all possible environmental conditions and cultural conditions. The phenotype may vary somewhat with variations in environmental conditions such as temperature, daylength and light intensity, without, however, any variance in genotype.

The following traits have been repeatedly observed and are determined to be the unique characteristics of 'Yellow San Remo Runner'. These characteristics in combination distinguish 'Yellow San Remo Runner' as a new and distinct *Chrysanthemum* plant:

1. Uniform, upright, outwardly spreading and mounding plant habit; moderately vigorous growth habit.
2. Freely branching habit; dense and full plant habit.
3. Uniform and freely flowering habit.
4. Large decorative-type inflorescences with bright yellow-colored ray florets.
5. Good garden performance.

Plants of the new *Chrysanthemum* differ primarily from the mutation parent, 'Bronze San Remo Runner', in ray floret color as plants of 'Bronze San Remo Runner' have greyed orange-colored ray florets.

Plants of the new *Chrysanthemum* can be compared to plants of *Chrysanthemum×morifolium* 'Red San Remo Runner', disclosed in a U.S. Plant patent application Ser. No. 13/815,609, filed concurrently. In side-by-side comparisons conducted in Staden-Oostnieuwkerke, Belgium, plants of the new *Chrysanthemum* differ primarily from plants of 'Red San Remo Runner' in ray floret color.

Plants of the new *Chrysanthemum* can also be compared to plants of *Chrysanthemum×morifolium* 'San Remo Runner', not patented. In side-by-side comparisons conducted in Staden-Oostnieuwkerke, Belgium, plants of the new *Chrysanthemum* differed from plants of 'San Remo Runner' primarily in ray floret color as plants of 'San Remo Runner' had pink-colored ray florets.

BRIEF DESCRIPTION OF THE PHOTOGRAPHS

The accompanying photographs illustrate the overall appearance of the new *Chrysanthemum* plant showing the colors as true as it is reasonably possible to obtain in colored reproductions of this type. Colors in the photographs may differ slightly from the color values cited in the detailed botanical description which accurately describe the colors of the new *Chrysanthemum* plant.

The photograph on the first sheet comprises a side perspective view of a typical flowering plant of 'Yellow San Remo Runner' grown in a container.

The photograph on the second sheet are close-up views of the upper and lower surfaces of typical inflorescences (left) and upper and lower surfaces of typical leaves (right) of 'Yellow San Remo Runner'.

DETAILED BOTANICAL DESCRIPTION

The aforementioned photographs and following observations and measurements describe plants grown during the summer and autumn in 19-cm containers in an outdoor nursery in Staden-Oostnieuwkerke, Belgium and under conditions and cultural practices typical of commercial *Chrysanthemum* production. During the production of the plants, day temperatures ranged from 10° C. to 25° C. and night temperatures ranged from 5° C. to 15° C. Plants were 5.5 months old when the photographs and description were taken. In the following description, color references are made to The Royal Horticultural Society Colour Chart, 2007 Edition, except where general terms of ordinary dictionary significance are used.

Botanical classification: *Chrysanthemum×morifolium* 'Yellow San Remo Runner'.

Parentage: Naturally-occurring whole plant mutation of *Chrysanthemum×morifolium* 'Bronze San Remo Runner', disclosed in U.S. Plant patent application Ser. No. 13/066,463.

Propagation:

*Type*.—Terminal vegetative cuttings.

*Time to initiate roots, summer*.—About 14 days at temperatures about 20° C.

*Time to initiate roots, winter*.—About 20 days at temperatures about 20° C.

*Time to produce a rooted young plant, summer*.—About 30 days at temperatures about 20° C.

*Time to produce a rooted young plant, winter*.—About 40 days at temperatures about 20° C.

*Root description*.—Fine, fibrous; light brown in color.

*Rooting habit*.—Freely branching; medium density.

Plant description:

*Plant and growth habit*.—Perennial *Chrysanthemum* plant with decorative type inflorescences; stems upright and outwardly spreading giving a uniformly mounding appearance to the plant; very freely branching habit with about 104 lateral branches developing per plant; pinching enhances lateral branch development; dense and full plant habit; moderately vigorous growth habit.

*Plant height*.—About 37.5 cm.

*Plant width*.—About 65 cm.

*Lateral branches*.—Length: About 12.1 cm. Diameter: About 3 mm. Internode length: About 2.2 cm. Strength: Strong. Aspect: Lateral branches positioned about 40° from the main stem. Texture: Densely pubescent; longitudinally ridged. Color: Close to 146B to 146C.

*Leaves*.—Arrangement: Alternate, simple. Length: About 3.8 cm. Width: About 2.2 cm. Shape: Obovate, three-lobed Apex: Apiculate. Base: Attenuate. Margin: Palmately lobed and coarsely dentate, sinuses divergent to parallel. Texture, upper surface: Sparsely pubescent. Texture, lower surface: Densely pubescent. Venation pattern: Pinnate. Color: Developing leaves, upper surface: Close to N137C. Developing leaves, lower surface: Close to 137B. Fully expanded leaves, upper surface: Close to 137B; venation, close to 144A. Fully expanded leaves, lower surface: Close to 137C; venation, close to 138B. Petioles: Length: About 5 mm. Diameter: About 2 mm. Texture, upper and lower surfaces: Densely pubescent. Color, upper and lower surfaces: Close to 144A.

Inflorescence description:

*Form and arrangement*.—Decorative inflorescence form; inflorescences borne on terminals above foliar plane; disc and ray florets arranged acropetally on a capitulum.

*Fragrance*.—Strongly fragrant, pungent.

*Flowering response*.—Under natural season conditions, plants begin flowering about October 10$^{th}$ in Belgium.

*Postproduction longevity*.—Inflorescences maintain good color and substance for about three weeks in an outdoor nursery; inflorescences not persistent.

*Quantity of inflorescences*.—About seven inflorescences develop per lateral branch; about 725 inflorescences develop per plant.

*Inflorescence buds*.—Height: About 7 mm. Diameter: About 7 mm. Shape: Globular. Color: Close to 137A; margins of phyllaries, close to 200A.

*Inflorescence diameter*.—About 4.2 cm.

*Inflorescence depth* (*height*).—About 2.2 cm.

*Disc diameter*.—About 5 mm.

*Receptacle diameter*.—About 3 mm.

*Receptacle height*.—About 3 mm.

*Receptacle color*.—Close to 144C.

*Ray florets*.—Number of ray florets per inflorescence: About 175 arranged in about nine whorls. Length: About 1.8 cm. Width: About 4 mm. Shape: Narrowly ovate to narrowly oblong. Apex: Obtuse to retuse. Base: Cuneate. Margin: Entire. Aspect: About 15° from vertical. Texture, upper surface: Smooth, glabrous; velvety; slightly longitudinally ridged. Texture, lower surface: Smooth, glabrous; slightly velvety; longitudinally ridged. Color: When opening, upper surface: Close to 3A. When opening, lower surface: Close to 3C. Fully opened, upper surface: Close to 3C; color becoming closer to 3D with development. Fully opened, lower surface: Close to 3D; color becoming closer to 2D with development.

*Disc florets*.—Number of disc florets per inflorescence: About 20 massed at the center of the inflorescence. Length: About 4 mm. Diameter: About 2 mm. Shape: Lower 75% fused into a tube; free apices are acute. Texture, inner and outer surfaces: Smooth, glabrous. Color: Towards the apex, close to 6C; mid-section, close to 150C; and towards the base, close to 145D.

*Phyllaries*.—Number of phyllaries per inflorescence: About 24 arranged in about three whorls. Length: About 6 mm. Width: About 3 mm. Shape: Ovate. Apex: Acute. Base: Cuneate. Margin: Entire. Texture, upper surface: Smooth, glabrous. Texture, lower surface: Pubescent. Color, upper surface: Close to 138A; margins, close to 199B. Color, lower surface: Close to 143C; margins, close to 199B.

*Peduncles*.—Length, terminal peduncle: About 8.2 cm. Length, fourth peduncle: About 13.9 cm. Length, seventh peduncle: About 15.1 cm. Diameter: About 1.5 mm. Aspect: Erect to about 35° from vertical. Strength: Strong. Texture: Densely pubescent. Color: Close to 138B.

*Reproductive organs*.—Androecium: Present only on disc florets. Number of stamens per floret: Five. Filament length: About 0.5 mm. Filament color: Close to 145D. Anther length: About 1 mm. Anther shape: Lanceolate. Anther color: Close to 13A. Pollen amount: Scarce. Pollen color: Close to 13B. Gynoecium: Present on ray and disc florets. Number of pistils per floret: One. Pistil length: About 3 mm. Style length: About 2.25 mm. Style color: Close to 150D. Stigma shape: Cleft, decurrent. Stigma color: Close to 5C. Ovary color: Close to 145D.

*Seeds and fruits*.—Seed and fruit development have not been observed on plants of the new *Chrysanthemum*.

Disease & pest resistance: Plants of the new *Chrysanthemum* have been observed not to be susceptible to Rust pathogens; resistance to pests and other pathogens common to *Chrysanthemum* plants has not been observed on plants of the new *Chrysanthemum* grown under commercial conditions.

Garden performance: Plants of the new *Chrysanthemum* have good garden performance, are hardy to USDA Hardiness Zones 7 to 8 and tolerate high temperatures of about 35° C.

It is claimed:

1. A new and distinct *Chrysanthemum* plant named 'Yellow San Remo Runner' as illustrated and described.

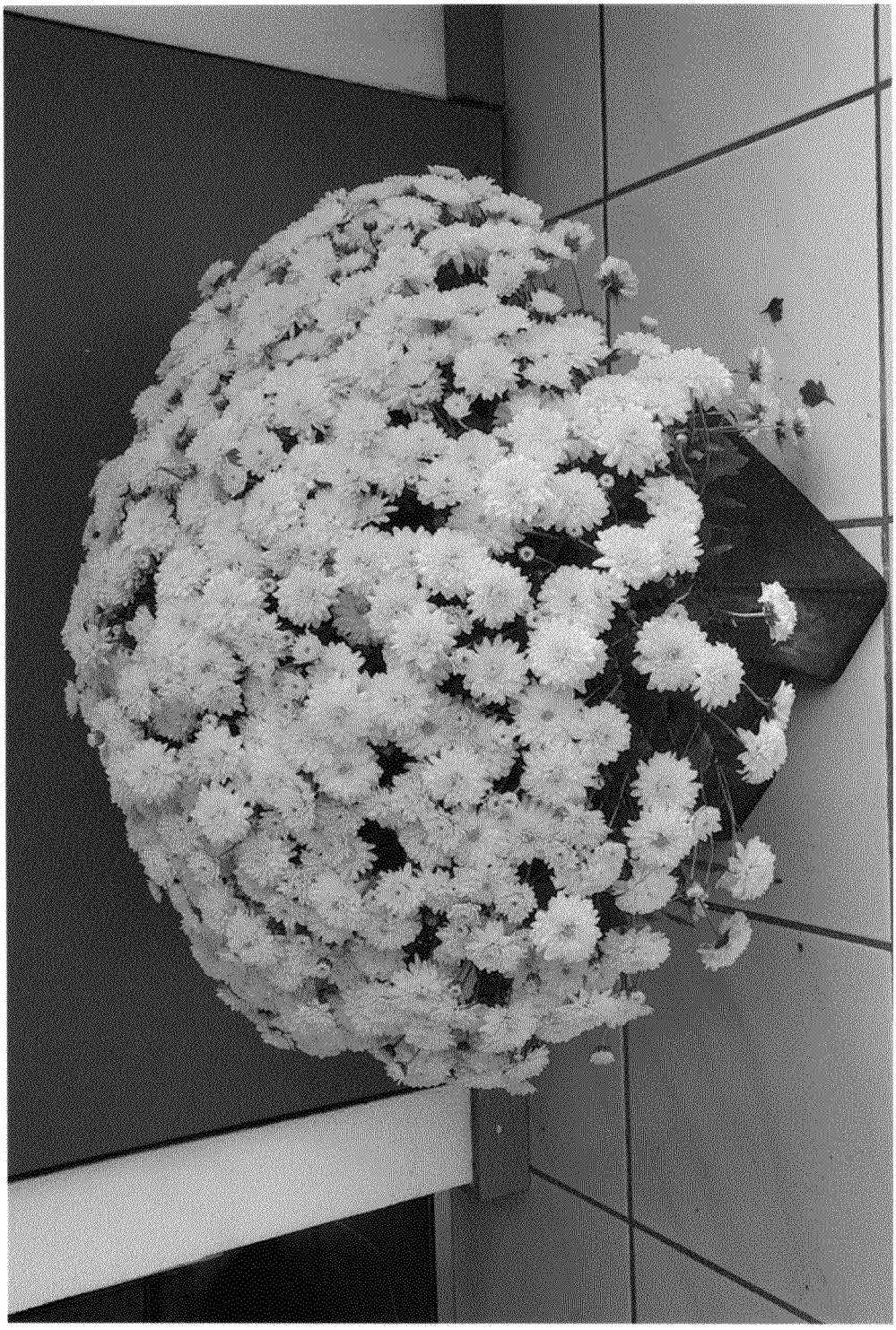

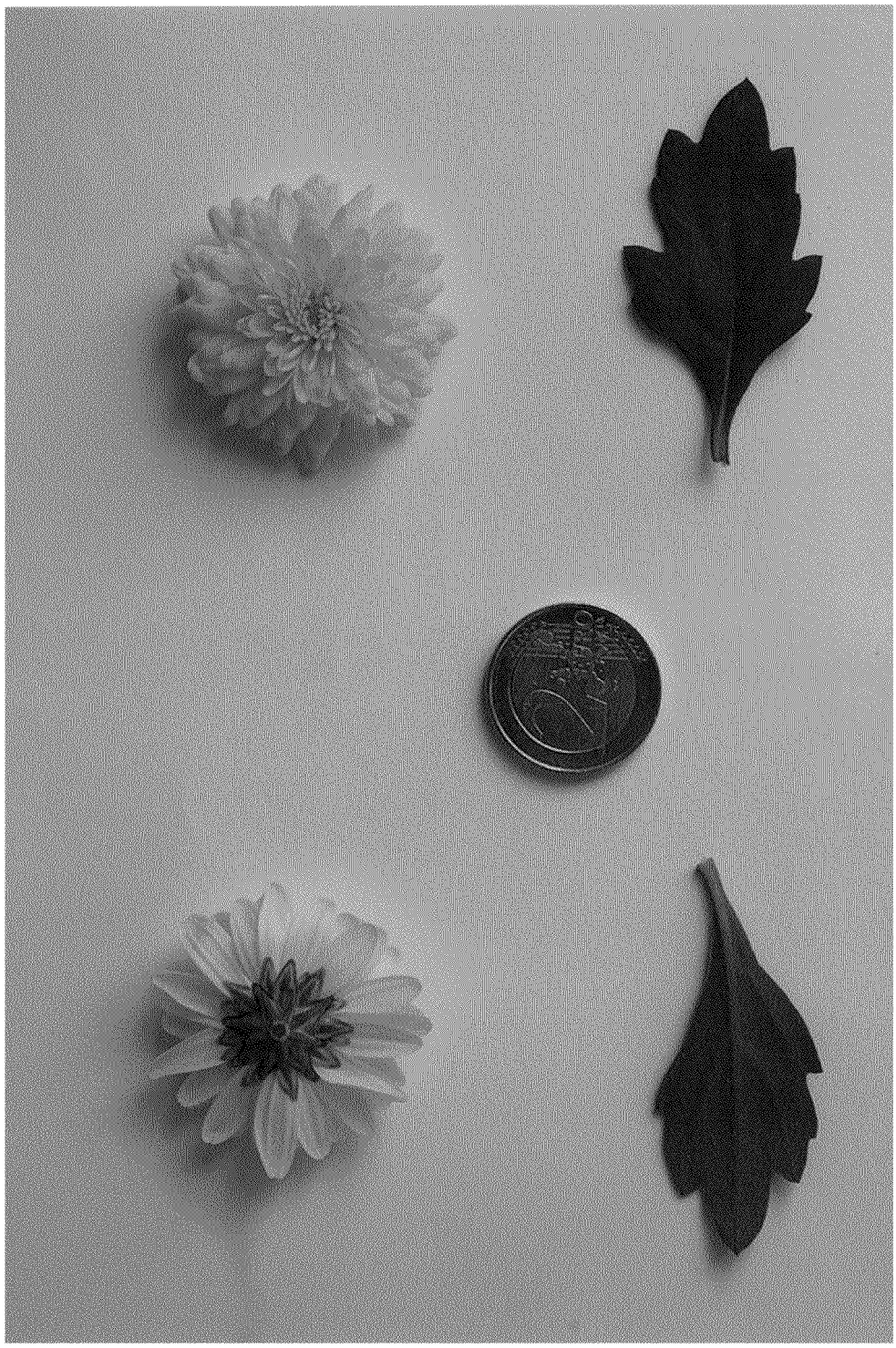

* * * * *